United States Patent
Lee et al.

(10) Patent No.: US 7,399,898 B2
(45) Date of Patent: Jul. 15, 2008

(54) SIMULATED MOVING BED ADSORPTIVE SEPARATION PROCESS FOR PREVENTING INCREASE IN PRESSURE DROP AND SYSTEM THEREOF

(75) Inventors: Jin Suk Lee, Seosan-shi (KR); Nam Cheol Shin, Seosan-shi (KR)

(73) Assignee: Samsung Petrochemicals Co., Ltd., Chungcheongnam-do (KR)

( * ) Notice: Subject to any disclaimer, the term of this patent is extended or adjusted under 35 U.S.C. 154(b) by 424 days.

(21) Appl. No.: 11/100,041

(22) Filed: Apr. 6, 2005

(65) Prior Publication Data

US 2005/0222482 A1    Oct. 6, 2005

(30) Foreign Application Priority Data

Apr. 6, 2004    (KR) .................. 10-2004-0023460

(51) Int. Cl.
    C07C 7/12    (2006.01)
    B01J 8/18    (2006.01)
    B01D 15/08   (2006.01)

(52) U.S. Cl. ................. 585/820; 422/139; 422/140; 210/657; 210/659

(58) Field of Classification Search ............. 585/820; 422/139, 140; 210/657, 659
See application file for complete search history.

(56) References Cited

U.S. PATENT DOCUMENTS

| | | | |
|---|---|---|---|
| 3,732,078 A * | 5/1973 | Kassarjian | 422/191 |
| 4,326,092 A   | 4/1982 | Neuzil | |
| 4,579,647 A * | 4/1986 | Smith | 208/111.01 |
| 5,382,747 A   | 1/1995 | Kulprathipanja | |
| 6,407,305 B1* | 6/2002 | Sohn | 585/820 |
| 6,429,346 B2* | 8/2002 | Hotier et al. | 585/475 |

* cited by examiner

*Primary Examiner*—Walter D. Griffin
*Assistant Examiner*—Lessanework T Seifu
(74) *Attorney, Agent, or Firm*—Gifford, Krass, Sprinkle, Anderson & Citkowski, P.C.

(57) ABSTRACT

Disclosed is a simulated moving bed (SMB) adsorptive separation system in which at least one component of a fluid mixture is brought into contact with a solid adsorbent and the adsorbed component is desorbed with a desorbent, wherein the improvement comprises an inert ball layer is formed on the upper part of the solid absorbent filled in the simulated moving bed.

8 Claims, 7 Drawing Sheets

(a)

(b)

SIMULATED MOVING BED ADSORPTIVE SEPARATION PROCESS FOR PREVENTING INCREASE IN PRESSURE DROP AND SYSTEM THEREOF

RELATED APPLICATION

This application claims priority of Korean Patent Application No. 10-2004-0023460 filed Apr. 6, 2004.

FIELD OF THE INVENTION

The present invention relates to an adsorptive separation process for separating each isomer from an isomeric mixture. More particularly, the present invention relates to an adsorptive separation process using simulated moving bed (SMB) adsorptive chromatography, which can prevent an increase in pressure drop in a reactor of the process.

BACKGROUND OF THE INVENTION

The generally used batch chromatography is a separation process using the principle of adsorption mechanism and is suitable for high-purity separation and laboratory analysis. Thus, it is widely used for the separation and purification of high-purity biosynthetic compounds, fine chemicals, food additives and the like. However, this separation process using batch chromatography has problems in that it requires the use of a large amount of solvents and is difficult to separate components when a difference in adsorption between the components is small. Furthermore, it is unsuitable for large-scale separation and continuous separation.

In an attempt to solve these problems, a true moving bed (TMB) adsorptive separation process is used. This TMB process utilizes the countercurrent concept, which is effectively applied in heat exchangers or extraction processes. In this TMB process, when flow is introduced to a fixed bed countercurrently to a moving bed so that a solution of a mixture to be separated is introduced into a column, a component having a strong adsorption property to the fixed bed will flow out of the column by the fixed bed flow while a component having low adsorption will move along the moving bed.

The TMB process has an advantage in that it allows pure separation of two components if they can be separated only at both ends of their concentration distribution curve, even when there is no great difference in resolution between the two components. However, the TMB process has shortcomings in that it requires the use of a larger amount of filler than that of the existing fixed-type separation process and is very difficult to be performed in normal conditions due to the friction and release of the filler. To overcome these shortcomings, a simulated moving bed (SMB) adsorptive separation process has been developed in which a adsorbent, as a fixed bed, is filled into a separation column, and ports located along the separation column are moved at given time intervals so as to simulate the countercurrent movement of the fixed bed.

The SMB process has been developed to solve a problem in the fixed-bed flow of the TMB process and is applied for the purification of p-xylene, separation of ethylbenzene, and preparation of chiral compounds from a mixture of aromatic hydrocarbons, and the like. This process is typically disclosed in U.S. Pat. Nos. 4,326,092 and 5,382,747, assigned to UOP Inc.

In the separation of p-xylene by the prior SMB process, high-temperature and high-pressure conditions need to be maintained in order to maintain adsorption/desorption rates at suitable levels and to maintain fluid at a liquid phase. Due to such process characteristics, the rate of fluid flowing through each bed can greatly change suddenly in a moment, thus making the flow of the fluid unstable. When eddy current flow occurs due to the instability of fluid flow, adsorbent particles in the upper portion of each bed will be fluidized so that fine particles will occur due to the friction between the adsorbent particles. These fine particles are built up in the upper portion of each bed so as to cause pressure drop, and particularly when the fine particles are locally concentrated in the upper portion of each bed without uniform distribution, a channeling phenomenon will occur to cause a further increase in pressure drop. This increase in pressure drop makes the system going beyond its mechanical limit. Also, increased channeling will have a fatal adverse effect on the purity and recovery of p-xylene separated.

Thus, in order to solve the above-described problems occurring in the prior SMB adsorptive process, the present inventors formed an inert ball layer in the upper portion of each bed, i.e., on an adsorbent layer, so as to prevent the fluidization of adsorbent particles in the upper portion of each bed, thereby completing the present invention.

SUMMARY OF THE INVENTION

An object of the present invention is to provide a new simulated moving bed adsorptive separation process which can prevent an increase in pressure drop.

Another object of the present invention is to provide a simulated moving bed adsorptive separation process which allows stabilization of fluid flow through each bed in an adsorption chamber so as to prevent the fluidization of adsorbent particles in the adsorbent layer.

Still another object of the present invention is to provide a simulated moving bed adsorptive separation system which can prevent the build-up of fine adsorbent particles occurring in the upper portion of the bed.

Yet another object of the present invention is to provide a new simulated moving bed absorptive separation system which can prevent a channeling phenomenon which can occur by localized build-up of fine particles in the upper portion of each bed.

To achieve the above objects, the present invention provides a simulated moving bed (SMB) adsorptive separation system, in which at least one component of a fluid mixture is brought into contact with a solid adsorbent, and the adsorbed component is desorbed with a desorbent, wherein the improvement comprises an inert ball layer is formed on the upper portion of the solid absorbent filled in the simulated moving bed.

According to the present invention, the inert ball layer is made of alumina, mulite or ceramic balls and formed to a thickness of about 2-3 cm on the absorbent layer. The diameter of the inert balls is preferably about 0.125-0.25 inches.

In addition, the present invention provides a simulated moving bed adsorptive separation process in which at least component of a fluid mixture is brought into contact with a solid adsorbent and the adsorbed component is desorbed with a desorbent, the method comprising the steps of: introducing a fluid mixture into an adsorption chamber (column) through an inlet port and multiple access lines connected to a rotary valve, so as to bring the fluid mixture into contact with an adsorbent layer formed in each bed within the adsorption chamber and with the inert ball layer formed on the adsorbent layer; discharging a raffinate mixture of a raffinate having relatively low adsorption and the desorbent in the bed through a raffinate outlet port into a raffinate column where the raffinate mixture is separated into a high-boiling desorbent and a low-boiling raffinate; recycling the desorbent to the bed for use as a desorbent; discharging the raffinate through a first drum; discharging an extract mixture of an extract having relatively high adsorption and the desorbent, through an extract outlet port into an extract column where the extract mixture is separated into a high-boiling desorbent and a low-boiling extract; recycling the extract to the desorbent inlet port for use as an additional adsorbent; and discharging the extract through a second drum, wherein the rotary valve rotates according to switching time so that the fluid mixture inlet port, the raffinate outlet port, the extract outlet port and the desorbent inlet port are connected to the adjacent multiple excess lines.

BRIEF DESCRIPTION OF THE DRAWINGS

In FIG. 4, (a) is a cross-sectional view of a formed adsorbent layer, and (b) is a cross-sectional view showing that a fine particle layer resulting from the fluidization of adsorbent particles caused by the flow of fluid has been formed on the adsorbent layer.

DETAILED DESCRIPTION OF THE PREFERRED EMBODIMENT

Figure 1:
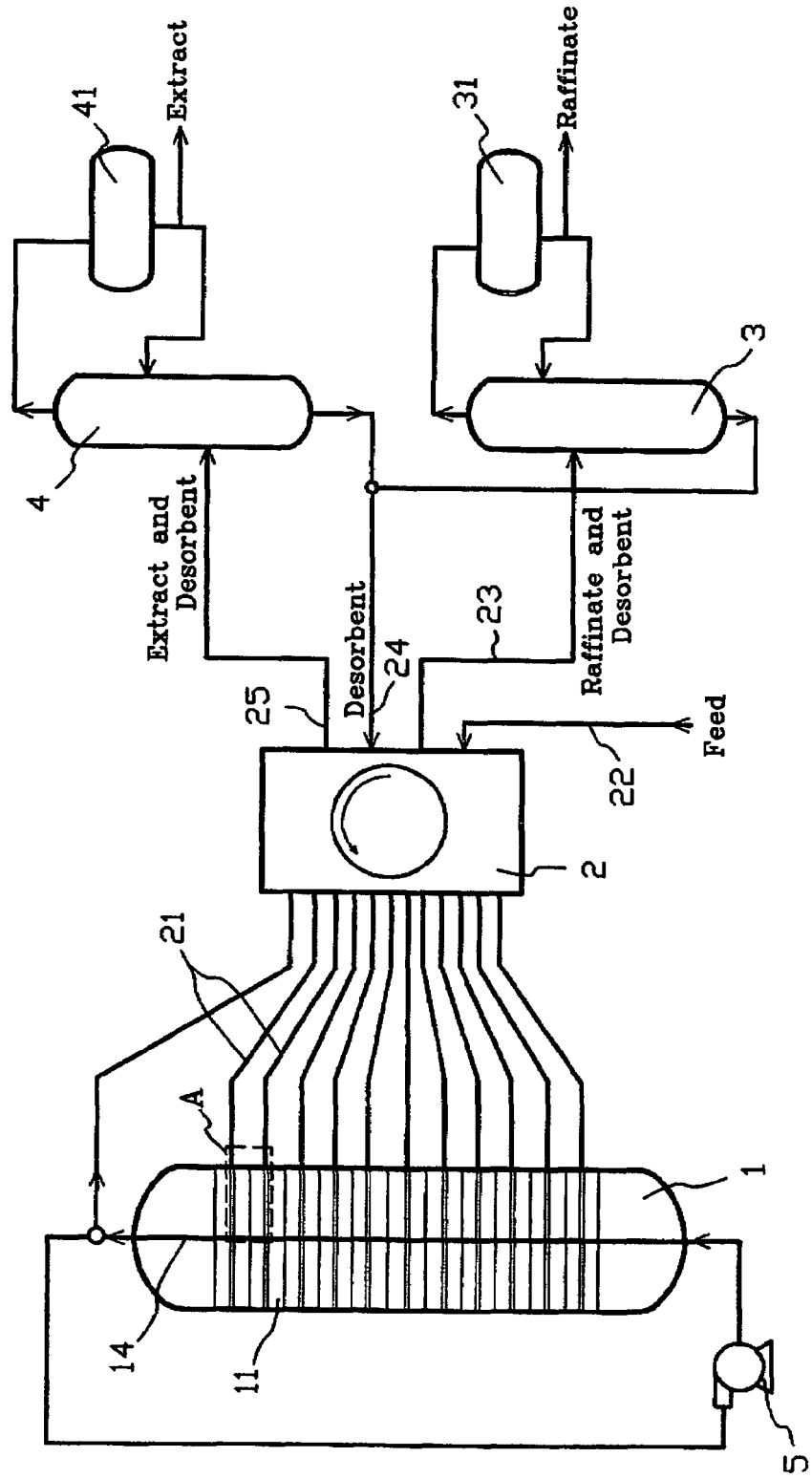
FIG. 1 schematically shows the SMB adsorptive separation process according to the present invention.

FIG. 1 schematically shows the SMB adsorptive separation process system.

In the SMB adsorptive separation system as shown in FIG. 1, a number of beds 11 are formed within adsorption chamber (column) 1, and an adsorbent layer is formed in each of the beds. Each bed in the adsorption chamber 1 is connected to rotary valve 2 through multiple access lines 21. In FIG. 1, although the number of the beds is 12 with one adsorption chamber shown, that is only for exemplification but not to be limited thereto. The actual system commonly has two adsorption chambers.

The rotary valve 2 connects fluid mixture inlet port 22, raffinate port 23, desorbent inlet port 24 and extract outlet port 25 to the multiple access lines 21. The fluid mixture inlet port 22 and the desorbent inlet port 24 are inlet ports, and the raffinate port 23 and the extract outlet port 25 are outlet ports. The detailed construction of the rotary valve 2 is well known to those having ordinary skill in the art.

A raffinate mixture discharged through the raffinate outlet port 23 is separated into a raffinate and a desorbent while passed to raffinate column 3, and then the raffinate is discharged through a first drum. The separated desorbent is recycled to the desorbent inlet port 24 for use as a desorbent.

An extract mixture discharged through the extract outlet port 25 is separated into an extract and a desorbent while passed to extract column 4, and then the extrace is separated through a second drum. The separated desorbent is recycled to the desorbent inlet port 24 for use as a desorbent.

In the SMB adsorptive separation process system according to the present invention, a number of the beds 11 are serially arranged in the elongate adsorption chamber 1. In the SMB adsorptive separation process as described in the present invention, fixed-bed flow does not substantially exist. At a given interval of switching time, the locations of the desorbent, extract, feed and raffinate ports are changed in the flow reaction of the moving bed so that the column is laid in a direction opposite to the flow direction of the moving bed with respect to each port. By making the simulated flow of fixed bed as such, flow countercurrent to the moving bed can be simulated. The absorbent used as the fixed bed is filled into the bed, and according to the present invention, the inert ball layer is formed on the filled adsorbent layer.

The locations of the desorbent, extract, feed (fluid mixture) and raffinate ports 22, 23, 24 and 25 are not continuously movable. However, as shown in FIG. 1, the multiple access lines 21 connected to each bed are provided so that each flow periodically moves to the adjacent line by the rotary valve 2 at a given interval of switching time. This allows the similar effect as a continuous process to be obtained. Thus, in the mixture introduced through the feed inlet port, a component having weak adsorption is passed through the moving bed and flows out through the raffinate outlet port, and a component having strong adsorption is adsorbed to the adsorbent in the each bed 11 of the chamber 1 and flows out through the extract outlet port 25 as the column relatively moves according to the switching at a given interval.

The adsorption chamber 1 has a central pipe 14 therein and the fluid mixture is circulated by means of pump 5.

Figure 2:
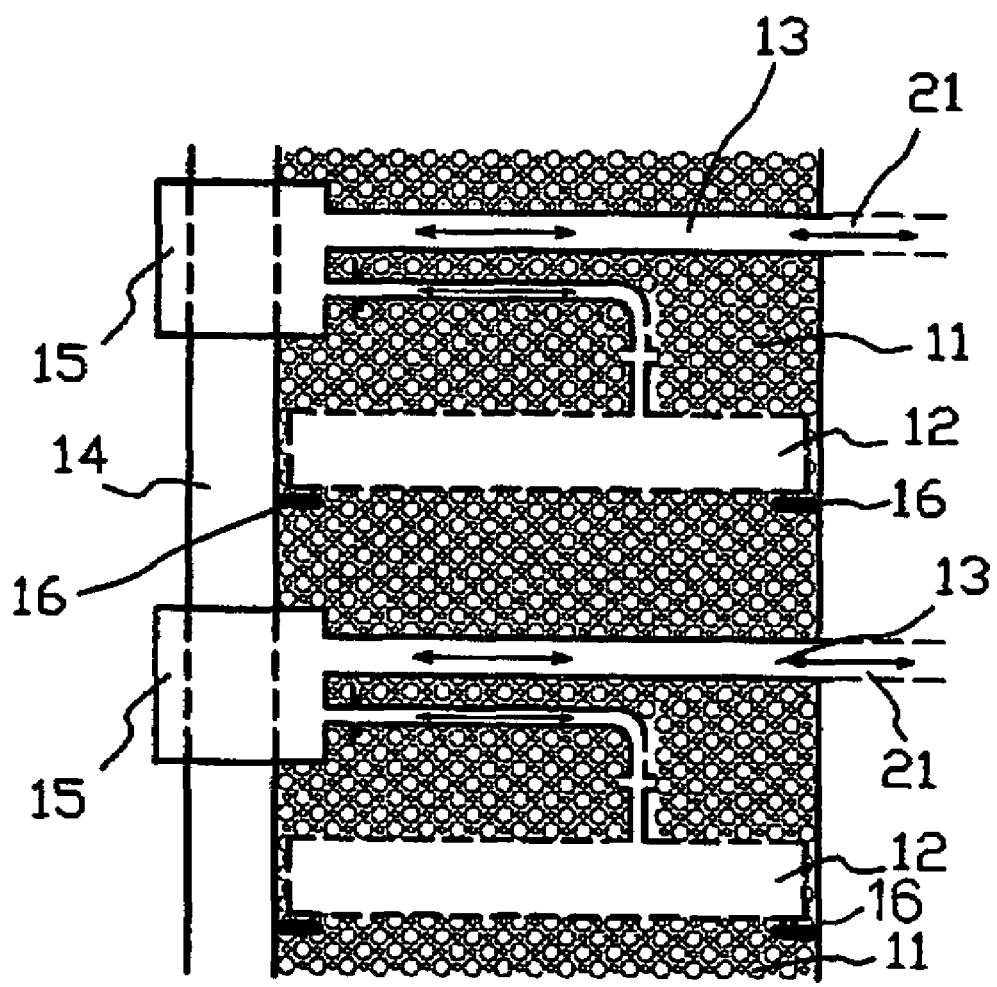
FIG. 2 is an enlarged cross-sectional view of portion "A" of FIG. 1 and schematically shows a bed in an absorption chamber of the SMB adsorptive separation system.
Figure 3:
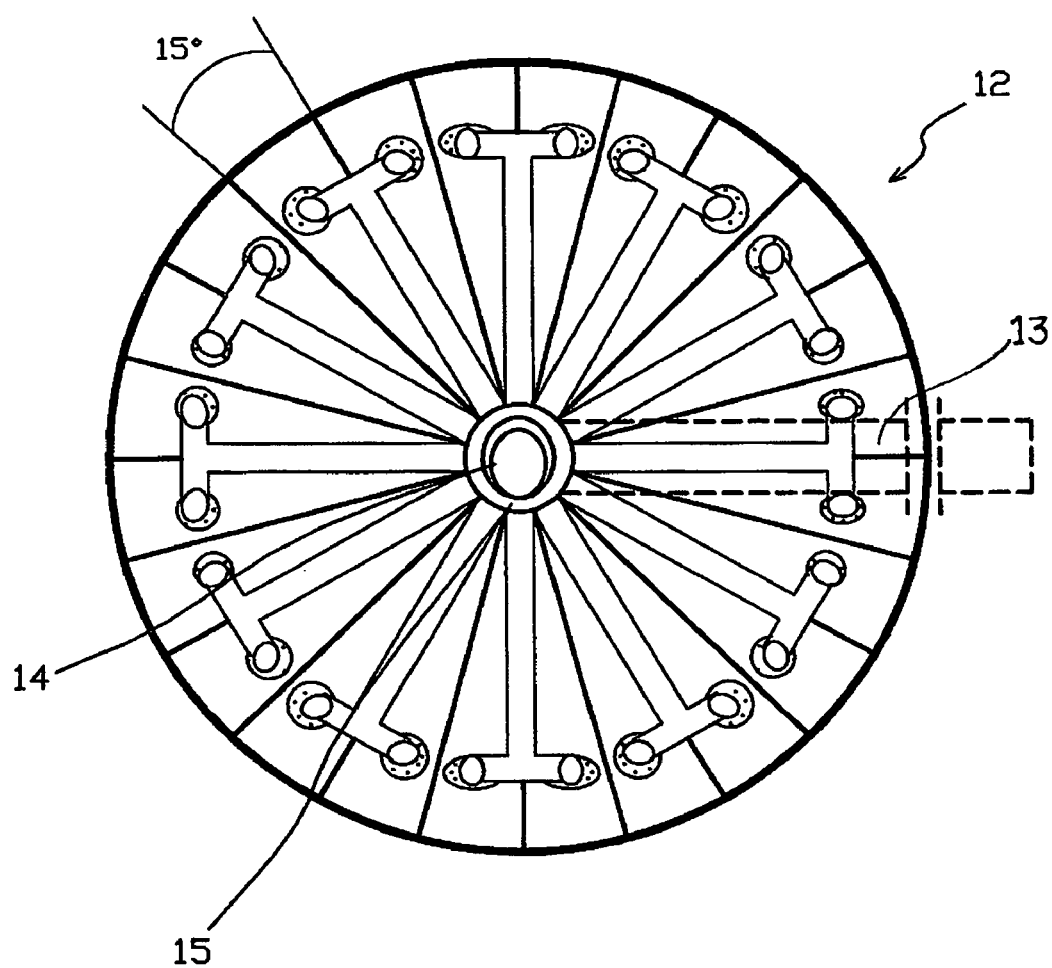
FIG. 3 is a schematic top view of a grid for supporting an adsorbent layer and an inert ball layer in a bed within the adsorption chamber.

FIG. 2 is an enlarged cross-sectional view of portion "A" of FIG. 1 and schematically shows a bed in the adsorption chamber of the SMB adsorptive separation process system. FIG. 3 is a schematic diagram of a grid for supporting an adsorbent layer in each bed within an adsorption chamber.

As shown in FIG. 2, in each bed 11, a disc-shaped grid 12 is disposed around central pipe 14, and on the grid, the adsorbent layer and the inert ball layer are formed. The grid is supported by support rings 16 formed on the outer wall of the central pipe 14 and the inner wall of the adsorption column 11, respectively. The fluid movement between the upper and lower beds is made through the grid 12.

Each grid 12 is connected to central pipe distributor 15 so that it is connected to the multiple access lines 21 through bed line 13. As shown in FIG. 3, the grid 12 according to the present invention is made of two folds of screen so that it allows passage of only liquid fluid. Thus, the grid 12 serves as a barrier in the bed 11 and comprises 24 pie-shaped pieces.

Figure 4:
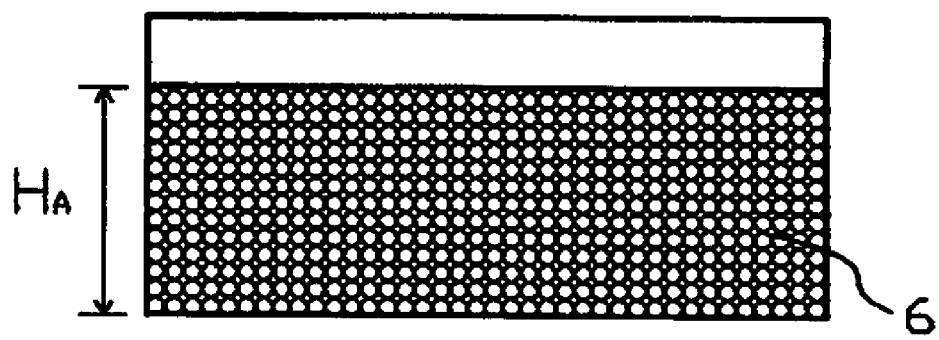
FIG. 4 schematically shows an absorbent layer formed on a grid in the prior SMB adsorptive separation process.
Figure 4:
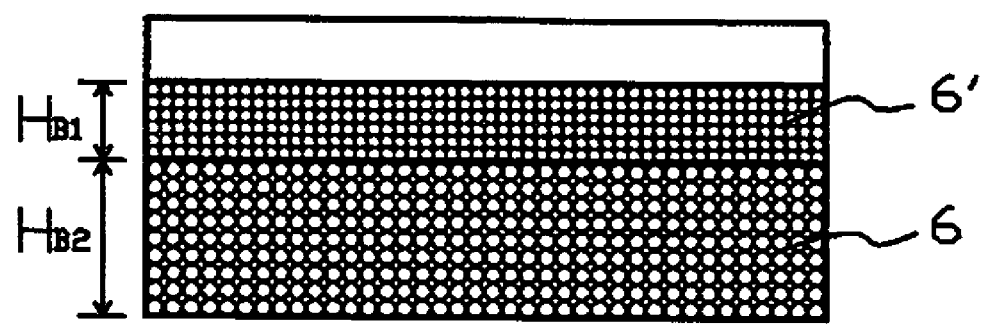

FIG. 4 schematically shows an absorbent layer formed on a grid in the prior SMB adsorptive separation process. In FIG. 4, (a) is a cross-sectional view of a formed adsorbent layer, and (b) is a cross-sectional view showing that a fine particle layer resulted from the fluidization of an adsorbent caused by the flow of fluid has been formed on the adsorbent layer.

As shown in FIG. 4(a), in the prior process, the absorbent is filled to height $H_A$. When fluid is introduced, the adsorbents 6 will be fluidized, and crushed by the friction therebetween. Thus, as shown in FIG. 4(b), fine adsorbent particles 6' will be built up to height $H_{B1}$. This build up of the fine particles will result in an increase in pressure drop within the adsorption chamber 1, and particularly when the fine particles are locally concentrated, a channeling phenomenon will occur to cause a further increase in pressure drop. The increase in pressure drop and the channeling phenomenon will have a fatal adverse effect on the purity and recovery of p-xylene in a separation process of p-xylene.

Figure 5:
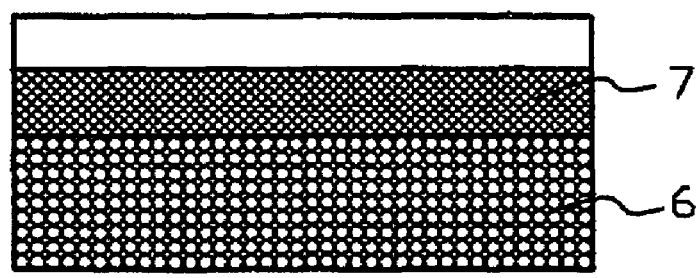
FIG. 5 is a schematic diagram showing an adsorbent layer formed on a grid in the inventive SMB adsorptive separation system and an inert ball layer formed on the adsorbent layer.

FIG. 5 is a schematic cross-sectional view showing adsorbent layer 6 formed on a grid in the inventive SMB adsorptive separation process system and inert ball layer 7 formed on the absorbent layer.

In the prior art, when fluid is introduced into the bed, the absorbent particles will be fluidized by eddy current occurring in the upper portion of the bed, so that they will be crushed by the friction therebetween and the resulting fine particles will be built up in the upper portion of the bed. This phenomenon occurring in the prior art is prevented by the inert ball layer 7 used in the present invention. In the prior art, in order to prevent the particle crushing from occurring due to the direct contact between the grid and the underlying adsorbent particles in the upper portion of the bed, the adsorbent particles were filled in such a manner that a space of about 4 cm on the absorbent layer is formed. However, this prior method has a problem in that the fluidization of the absorbent particles occurs. In the present invention, the inert ball layer is formed on the absorbent layer, and does not hinder fluid from contacting with the adsorbent. At the same time, this inert ball layer has the effects of pressing the underlying adsorbent and uniformly redistributing the flow of fluid into the bed. Thus, it can effectively prevent the absorbent particles from being fluidized by the fluid flow.

Concrete examples of inert balls used in the present invention include alumina, mulite, ceramic balls and the like. The alumina balls are preferably used.

The inert ball layer of the present invention is preferably formed on the absorbent layer to a thickness of about 2-3 cm, and the diameter of the inert balls is preferably in a range of about 0.125-0.25 inches in view of the diameter of the adsorbent.

Hereinafter, the adsorptive separation process according to the present invention will be described in detail with reference to FIG. 1.

First, the inert ball layer is formed on the absorbent layer formed in each bed 11 within the adsorption bed 1. The feed is introduced into the adsorption bed 1 through the feed inlet port 22 and the multiple access lines 21 connected to the rotary valve 2. The introduced material is brought into contact with the adsorbent filled in each bed 11 within the adsorption chamber. In the bed, a raffinate mixture of a raffinate having relatively low adsorption and a desorbent is discharged through the raffinate outlet port 23 into the raffinate column 3 where the raffinate mixture is separated into a high-boiling desorbent and a low-boiling raffinate. The separated desorbent is recycled to the bed through the desorbent inlet port 24 for use as a desorbent, and the raffinate is discharged through the first drum 31.

In the bed, an extract mixture of an extract having relatively strong adsorption and the desorbent is discharged through the extract outlet port into the extract column 4 where the extract mixture is separated into a high-boiling desorbent and a low-boiling extract. The separated desorbent is recycled to the desorbent inlet port 24 for use as an additional desorbent, and the extract is discharged through the second drum 41. The feed inlet, raffinate outlet, extract outlet and desorbent inlet ports connected to each bed 11 are connected to the adjacent multiple access lines as the rotary valve rotates according to the switching time.

The above-described problems occurring in the prior SMB adsorptive separation process can be solved by forming the inert ball layer on the adsorbent layer 6 of each bed. This inert ball layer 7 does not hinder fluid from contacting with the adsorbent and at the same time, can stabilize the flow of fluid so as to prevent the fluidization of the absorbent and the generation of fine particles, which are caused by the fluid flow. This can prevent an increase in pressure drop or the channeling phenomenon resulting from fine particles.

Hereinafter, the present invention will be described in more detail by the following example. It is to be understood, however, that the following example is given for illustrative purpose only and is not construed to limit the scope of the present invention.

EXAMPLE

In Example of the present invention and Comparative Example, tests to examine the fluidization of adsorbent particles filled in a bed were performed in the following manner.

First, a pipette was filled with adsorbent particles on which inert balls were filled to a thickness of 0.5 cm. The top of the pipette was connected with a tap, and water flowed through the pipette. The flow rate of water was about 2 cm/s, and water dropping from the bottom of the pipette was received in a measurement cylinder so as to examine the amount of water received per unit time. During this procedure, the fluidization of adsorbent particles in the upper portion of the bed was observed. A photograph showing the observation result is shown in FIG. 6.

COMPARATIVE EXAMPLE

Only an adsorbent layer was formed in a pipette without the formation of an inert ball layer. Then, the test was performed in the same manner as in Example, and the fluidization of the adsorbent particles was observed. A photograph showing the observation result is shown in FIG. 7.

Figure 6:
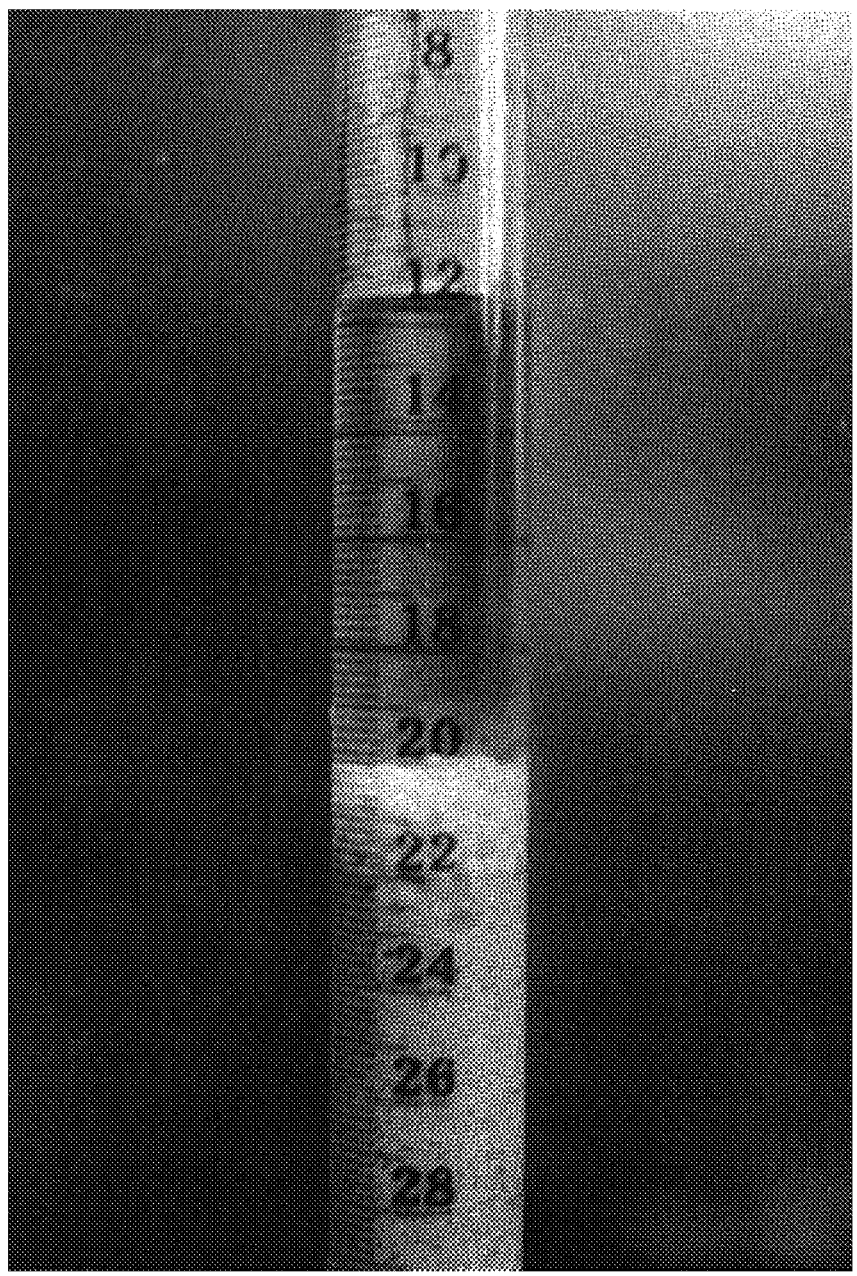
FIG. 6 is a photograph showing the result of fluidization test of adsorbent particles in an absorbent layer according to Example of the present invention.
Figure 7:
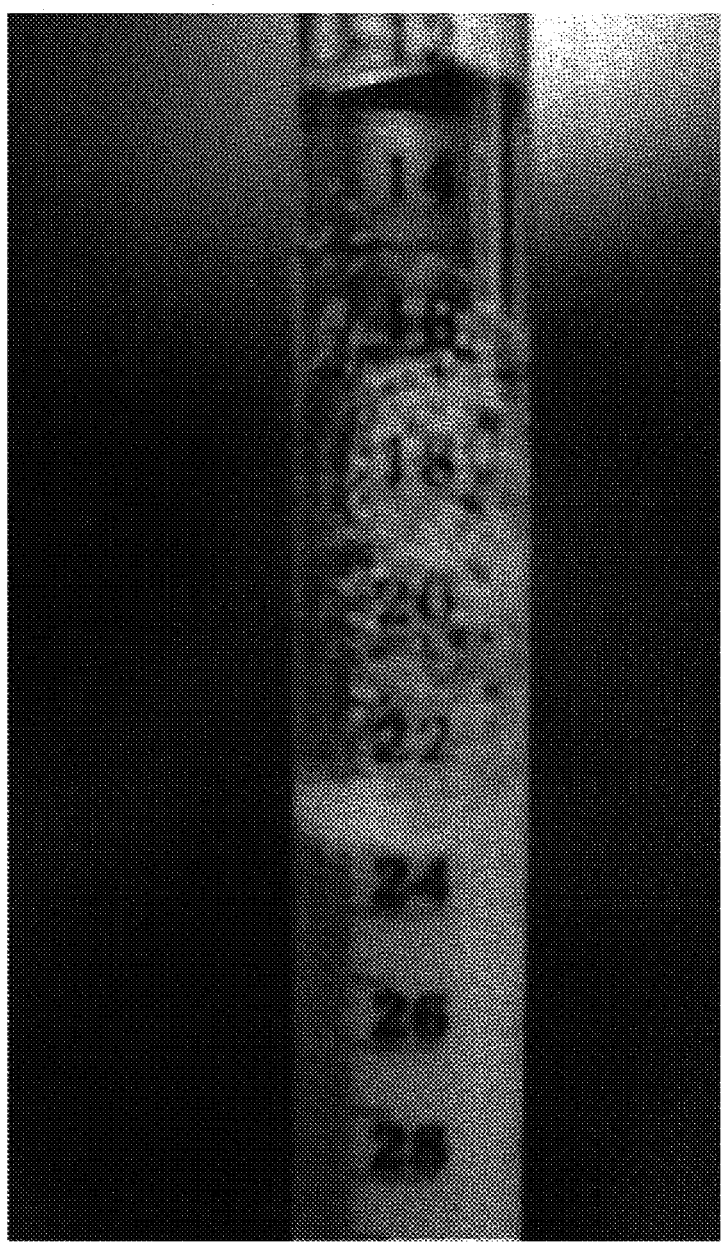
FIG. 7 is a photograph showing the result of fluidization test of adsorbent particles in an absorbent layer according to Comparative Example of the present invention.

As can be seen in FIGS. 6 and 7, the inert ball layer in the bed according to the present invention can prevent the fluidization of the adsorbent particles resulting from the flow of the fluid.

Although a preferred embodiment of the present invention has been described for illustrative purposes, those skilled in the art will appreciate that various modifications, additions and substitutions are possible, without departing from the scope and spirit of the invention as disclosed in the accompanying claims.

The invention claimed is:

1. In a simulated moving bed (SMB) adsorptive separation system for a liquid in which at least one component of a liquid mixture is brought into contact with solid adsorbent of an adsorbent layer formed in the bed and the adsorbed component is desorbed with a desorbent, an improvement comprising an inert ball layer having a thickness of from about 2 to 3 centimeters formed on one side of the absorbent layer.

2. The system as defined in claim 1, wherein said inert ball layer is formed with alumina, mulite, or ceramic balls.

3. The system as defined in claim 2, wherein said inert balls have about 0.125-0.25 inches of diameter.

4. In a process for separating a liquid mixture using a simulated moving bed (SMB) process by bringing at least one component of the liquid mixture into contact with solid adsorbent of an adsorbent layer formed in the bed and desorbing the adsorbed component with a desorbent, the process comprising the steps of:

introducing a liquid mixture into an adsorption chamber through an inlet port and multiple access lines connected to a rotary valve;

contacting the liquid mixture with an adsorbent layer formed in each bed and with an inert ball layer having a thickness of from about 2 to 3 centimeters formed on one side of the adsorbent layer;

discharging a raffinate mixture of a raffinate having relatively low adsorption ratio and the desorbent in the bed through a raffinate outlet port; and discharging an extract mixture of an extract having relatively high adsorption ratio and the desorbent from the bed, through an extract outlet port;

wherein the rotary valve is operated in accordance with predetermined switching time so that the fluid mixture inlet port, the raffinate outlet port, the extract outlet port and the desorbent inlet port are connected to the adjacent multiple excess lines.

5. The process as defined in claim 4, further comprising the steps of:

separating the discharged raffinate mixture into a high-boiling desorbent and a low-boiling raffinate in a raffinate column;

recycling the desorbent to the bed for use as a desorbent; and discharging the raffinate through a first drum.

6. The process as defined claim 4, further comprising the steps of:

separating the extract mixture into a high-boiling desorbent and a low-boiling extract;

recycling the extract to the desorbent inlet port for use as an additional adsorbent; and discharging the extract through a second drum.

7. The process as defined in claim 4, wherein said inert ball layer is formed with alumina, mulite, or ceramic balls.

8. The process as defined in claim 4, wherein said inert balls have about 0.125-0.25 inches of diameter.

* * * * *

UNITED STATES PATENT AND TRADEMARK OFFICE
CERTIFICATE OF CORRECTION

PATENT NO. : 7,399,898 B2  Page 1 of 1
APPLICATION NO. : 11/100041
DATED : July 15, 2008
INVENTOR(S) : Jin Suk Lee et al.

It is certified that error appears in the above-identified patent and that said Letters Patent is hereby corrected as shown below:

Column 1, line 53, replace "a adsorbent" with --an adsorbent--

Column 4, line 3, replace "extrace" with --extract--

Signed and Sealed this

Twenty-first Day of October, 2008

JON W. DUDAS
*Director of the United States Patent and Trademark Office*